(12) United States Patent
Quimby, Jr. et al.

(10) Patent No.: US 6,455,036 B1
(45) Date of Patent: *Sep. 24, 2002

(54) GRANULATED FORMULATION AND METHOD FOR STABILIZING BIOCONTROL AGENTS

(75) Inventors: Paul C. Quimby, Jr.; Anthony J. Caesar; Jennifer L. Birdsall, all of Bozeman, MT (US); William J. Connick, Jr., New Orleans, LA (US); Clyde D. Boyette, Leland, MI (US); Nina K. Zidack; William E. Grey, both of Bozeman, MT (US)

(73) Assignees: The United States of America as represented by the Secretary of Agriculture, Washington, DC (US); Research and Development Institue, Inc., Bozeman, MT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 843 days.

(21) Appl. No.: 08/695,249

(22) Filed: Aug. 8, 1996

(51) Int. Cl.[7] .......................... A01N 63/00; C12N 7/00; C12N 1/14; C12M 7/01

(52) U.S. Cl. .................. 424/93.1; 424/93.3; 424/93.46; 424/93.4; 424/404; 424/405; 424/407; 514/44; 435/235.1; 435/238; 435/252.5; 435/254.1; 435/254.2; 435/255.1; 435/258.1; 435/243

(58) Field of Search ................................ 424/93.1, 93.3, 424/93.46, 93.4, 404, 405, 406, 407; 514/44; 435/235.1, 238, 252.5, 243, 254.1, 254.2, 255.1, 258.1

(56) References Cited

U.S. PATENT DOCUMENTS

| | | | |
|---|---|---|---|
| 4,530,834 A | | 7/1985 | McCabe et al. ............... 424/93 |
| 4,718,935 A | | 1/1988 | Walker et al. .................. 71/79 |
| 4,767,441 A | | 8/1988 | Walker et al. .................. 71/79 |
| 4,818,534 A | * | 4/1989 | Levy .......................... 424/404 |
| 4,859,377 A | * | 8/1989 | Shasha et al. ................ 264/4.1 |
| 5,061,697 A | | 10/1991 | Shasha et al. ................ 514/60 |
| 5,074,902 A | | 12/1991 | Connick, Jr. et al. ............ 71/79 |
| 5,358,863 A | | 10/1994 | Quimby, Jr. et al. ........ 435/178 |

OTHER PUBLICATIONS

Webster's II New Riverside University Dictionary, Soukhanov et al. (eds.), 1984, Houghton Mifflin Company, Boston, MA, p. 67.*

McGuire, M. R., et al., "Sprayable Self–Encapsulating Starch Formulations for *Bacillus thuringiensis*", *Journal of Economic Entomology*, vol. 83, No. 5, Oct. 1990, pp. 1813–1817.

Amsellem, Z., et al., "Complete Abolition of High Inoculum Threshold of Two Mycoherbicides (*Alternaria cassiae* and *A. crassa*) When Applied in Invert Emulsion", *Phytopathology*, vol. 80, No. 10, 1990, pp. 925–929.

Mugnier, J., et al., "Survival of Bacteria and Fungi in Relation to Water Activity and the Solvent Properties of Water in Biopolymer Gels", *Applied and Environmental Microbiology*, Jul. 1985, vol. 50, No. 1, pp. 108–114.

Leslie, Samuel B., et al., "Trehalose and Sucrose Protect Both Membranes and Proteins in Intact Bacteria during Drying", *Applied and Environmental Microbiology*, Oct. 1995, vol. 61, No. 10, pp. 3592–3597.

Caesar, A.J., et al., "Effect of Conditioning, Betaine, and Sucrose on Survival of Rhizobacteria in Powder Formulations", *Applied and Environmental Microbiology*, Jan. 1991, vol. 57, No. 1, pp. 168–172.

Connick, Jr., W. J., et al., "Water Activity and Other Factors that Affect the Viability of *Colletotrichum truncatum* Conidia in Wheat Flour–Kaolin Granules ('Pesta')", *Biocontrol Science and Technology*, 1996, 6, pp. 277–284.

Connick, Jr., W.J., et al., ""Pesta": New Granular Formulations for *Steinernema carpocapsae*", *Journal of Nematology*, vol. 25, No. 2, Jun. 1993, pp. 198–203.

Connick, Jr., William J., et al. . "Formulation of Mycoherbicides Using a Pasta–like Process", *Biological Control*, 1, 1991, pp. 281–287.

Womack, Jonathan G., et al., "A Vegetable Oil–Based Invert Emulsion for Mycoherbicide Delivery", *Biological Control*, 6, 1996, Article 0003, pp. 23–28.

Zidack, N.K., et al., "An Oil/Starch/Sugar Encapsulation Method Suitable for Gram–Negative Bacteria and Other Microbes", Abstract of Presentations, 1995 APS Annual Meeting, Presented 08/12–16, 1995, Pittsburgh, PA, *Phytopathology*, vol. 85., No. 10, 10/95.

Norman, David J., et al., "Development of *Colletotrichum gloeosporiodes* f. Sp. clidemiae and *Septoria passiflorae* into Two Mycoherbicides with Extended Viability", *Plant Disease*, Oct. 1995, vol. 79, No. 10, pp. 1029–1032.

* cited by examiner

*Primary Examiner*—Christopher S. F. Low
(74) *Attorney, Agent, or Firm*—M. Howard Silverstein; Curtis P. Ribando; John D. Fado

(57) ABSTRACT

A stabilized, granular, biocontrol agent formulation for agricultural pests relies upon a combination of a water absorbent material, a membrane stabilization agent, and a granulating agent to achieve the desired stability and free-flowing properties. The granular product is easily prepared by simple mixing and can be readily rehydrated into a sprayable composition.

18 Claims, No Drawings

GRANULATED FORMULATION AND METHOD FOR STABILIZING BIOCONTROL AGENTS

BACKGROUND OF THE INVENTION

1. Field of the Invention

With the increase in emphasis within the agricultural community on using biocontrol agents as substitutes for chemicals in the control of weeds, insects, and other pests, considerable research has been directed to compositions and mechanisms for delivering the agents in a way which will preserve their effectiveness in the field. This invention relates to a novel granular formulation of biocontrol agents.

2. Description of the Prior Art

Dunkle et al. [*Environ. Entomol.* 17:20–126 (1988)] and U.S. Pat. No. 4,859,377 show a granular formulation of *Bacillus thuringiensis* (*B.t.*) encapsulated within a starch matrix. The advantage of this product over prior formulations was that it allowed incorporation of various additives such as sunlight protectors and palatable feeding stimulants, thereby reducing the amount of active ingredient necessary for control. Trimnell et al. [*J. Controlled Release* 7: 263–268 (1988)] reported a sprayable herbicide formulation utilizing pregelatinized corn starch and flour. These sprays were designed to coat plant leaves with a thin film of material which would autoencapsulate (encapsulate the active agent in situ) upon drying and thereby allow sustained release of active ingredient. However, within 2–3 days after application, these films were found to peel away from the plant leaves. In general, sprayable formulations of *B.t.* lose activity within 2–4 days following application to plant foliage in the field [Morris, *Can. Ent.* 115: 1215–1227 (1983); Beegle et al., *Environ. Entomol.* 10: 400–401 (1981); Leong et al., *Environ. Entomol.* 9: 593–599 (1980)].

Shasha et al. [U.S. Pat. No. 5,061,697 and *J. Econ. Entomol.* 83(5): 1813–1817 (1990)], teach sprayable, starch-based formulations for autoencapsulating biological control agents, such as pathogenic bacteria and viruses. These compositions incorporate a sugary material to promote adherence of the encapsulated agent to treated foliage.

Walker et al., U.S. Pat. Nos. 4,718,935 and 4,767,441, teach pelletization of infective propagules of fungal plant pathogens using aqueous solutions of sodium alginate and calcium chloride. This system relies upon the ability of the fungus to grow through the gelled alginate matrix to the pellet surface, where spores of the fungus are produced and released to the target plant.

Quimby et al. (U.S. Pat. No. 5,358,863) teach forming granules by encapsulating bacteria, fungi or nematodes useful for controlling agricultural pests in alginate, starch or wheat gluten, and then coating the granules with an invert oil that forms a water-in-oil emulsion and an absorbent for the oil to make the coated granules free-flowing. See also Amsellem et al. [*Phytopathology*, 80(10):925–929 (1990)]. The oil slows the drying of the organisms to maintain their vitality. The resulting products are applied by spraying through large-orifice nozzles.

McCabe et al. (U.S. Pat. No. 4,530,834) teach the preparation of entomopathogenic fungal insect control agents by culturing mycelia in a suitable medium, harvesting the growing mycelia, treating the mycelia with a protective agent such as maltose or glucose, and drying the product.

Mungier et al. [*Appl. and Environ. Micro.*, 50(1): 108–114 (1985)] presents a study on the survival of bacteria and fungi in relation to water activity and the solvent properties of water in biopolymer gels. This reference shows that cells survive at a water activity ($a_w$ 0.069 and below and die at an $a_w$ above that.

Caesar et al. [*Appl. and Environ. Micro.*, 57(1): 168–172 (1991)] demonstrated that strains of Pseudomonas and members of the family Enterobacteriaceae could be conditioned for improved shelf life in simple dry formulations by aging, exposure to osmotica, or growth on media amended with sucrose or betaine. Similarly, Leslie et al. [*Appl. and Environ. Micro.*, 61(10): 3592–3597 (1995)] teach that when *E. coli* and *B.t.* were dried in the presence of trehalose or sucrose, their survival rate was greatly enhanced over organisms dried without the sugars. The increased survivability is attributed to lowering of the transition temperature ($T_m$) of the dry membranes by replacement of the water between the membrane lipid headgroups with the disaccharide.

Connick et al. [U.S. Pat. No. 5,074,902 and *Biological Control* 1: 281–287 (1991)] teach encapsulation of fungal propagules in a wheat gluten matrix, resulting in a pasta-like product referred to as "Pesta". Pesta is prepared from a dough of wheat flour, kaolin filler, fungus and water. The dough is rolled into a thin sheet, air-dried, and cut with a pasta maker or ground into granules. Upon application of the product to the soil, the fungi grow and sporulate on the granules. The Pesta technology has also been shown by Connick et al. [*Journal of Nematology* 25(2):198–203 (1993)] to be useful for the encapsulation of nematodes (*Steinernema carpocapsae*). In *Biocontrol Science and Technology* 6:277–284 (1996), Connick et al. show that, at relatively high $a_w$, sucrose helps maintain Colletotrichum sp. conidia viability in Pesta granules during storage.

SUMMARY OF THE INVENTION

We have now unexpectedly discovered a simple and inexpensive procedure for preparing a stabilized, granular, biocontrol agent which can optionally be formulated as a rehydratable sprayable composition. The invention is applicable to a wide variety of living, pathogenic biocontrol agents useful in the management of all types of agricultural pests.

In accordance with this discovery, it is an object of the invention to provide a facile, universal, and industrially acceptable procedure for granular formulation of sensitive biocontrol agents.

It is also an object of the invention to formulate biocontrol agents without loss of viability and with a high degree of stability under storage and field conditions.

Another object of the invention is to prepare biocontrol products that are clean, easy to handle, and have relatively low crop phytotoxicity.

A further object of the invention is to package biocontrol agents into formulations that can be applied with conventional agricultural sprayers.

Other objects and advantages of this invention will become readily apparent from the ensuing description.

DETAILED DESCRIPTION OF THE INVENTION

The primary components of the formulations of the invention include (1) a biocontrol agent, (2) a water absorbent material, (3) a membrane stabilization agent, and (4) a granulating agent. Oil is an optional primary component.

The Biocontrol Agent

The biocontrol agents contemplated for use herein include without limitation all bacteria, fungi, yeasts, viruses, microsporidians, protozoa, nematodes and other such organisms that are pathogenic toward target pests. Of course, any component of the organism or stage of its life cycle which is infective to the host upon contact or ingestion is considered to be within the scope of the invention. For instance, in the case of *B.t.*, the vegetative cells, spores, and proteinaceous crystals are all effective in directly or indirectly killing host insects susceptible to *B.t.* It is also known that naturally occurring and synthetic vectors such as plasmids, phages, and various DNA/RNA constructs have potential for functionally modifying higher organisms, and therefore are also included herein as being within the scope of the term "biocontrol agent." Examples of other agronomically important pest pathogens besides *B.t.*, without limitation thereto include: other entomopathogenic bacteria such as *B. sphaericus*, and *B. popillae*; plant pathogenic bacteria, such as Pseudomonas spp. and Agrobacterium; plant pathogenic fungi, such as Sclerotinia, Rhizoctonia, Fusarium, Alternaria, Colletotrichum, and Sclerotium; entomopathogenic fungi, such as Pandora, Beauveria and Conidiobolus and the yeasts; entomopathogenic viruses, such as *Autographa californica* nuclear polyhedrosis virus, and Heliothis spp. virus; microsporidians such as *Vairimorpha necatrix* and *Nosema locustae*, as well as the nematode *Steinernema carpocapsae* and the gall-forming nematode *Subanguina picridis*.

The biocontrol agents of the invention are normally propagated by cultivation in a suitable aqueous medium and then recovered as a concentrated suspension of the biocontrol agent. Typically, these suspensions will comprise about 40–95% water. The Water Absorbent Material Suitable water absorbent materials are those which are capable of absorbing several times their own weight in water, preferably, at least about 100 times their own weight in substantially pure water. Most notable are the starch polyacrlonitrile graft copolymers (e.g. the composition of U.S. Pat. No. 3,935,099, herein incorporated by reference) and similar starch graft copolymers which are commercially known by names such as "Super Slurper", Water-lock®, etc. Upon absorbing water or other aqueous liquids, these materials swell into amorphous gels which tenaciously retain the absorbed water.

The amount of water absorbent material should be sufficient to absorb, and thereby bind, the free (available) water in the suspension of biocontrol agent. Typically, the ratio of water absorbent material to available water in the suspension would be on the order of about 1:5 to about 1:100, preferably about 1:10. In terms of the total weight of the final product, the water absorbent should constitute about 5–16% by weight. The skilled artisan will appreciate that salts in the suspension of the organism as well as other components already present in the formulation mixture at the time of addition of the absorbent material may reduce the inherent absorbancy of the material, requiring amounts in excess of that required for absorbing an equivalent amount of purified water. The relatively high absorbencies of these materials allows for binding of the free water using a relatively minor amount of this component, thereby permitting the formulation to accommodate effective amounts of the other components.

The Membrane Stabilization Agent

The principal function of the membrane stabilization agent is to bring the biocontrol agent to an immediate state of physiological quiescence and allow the organism to survive for long periods of time, even under adverse conditions. The preferred stabilization agent is sucrose; though it is envisioned that other disaccharides, such as trehalose, which have a similar capacity for reducing water availability could also be used. It is important that the membrane stabilization agent also have the property of forming a nongummy dough when mixed with the biocontrol agent and the water absorbent material described above.

The amount of the membrane stabilization agent should be in the range of about 50 mM to about 1 M, or about 10–65% by dry weight of the complete formulation. At 60% sucrose, the water potential of the formulation drops to at least −75 bars.

The Granulating Agent.

After the primary components heretofore described are blended into a dough, it is necessary to mix the dough with a granulation agent which causes the dough to break into small granules or "crumbs" and renders the product flowable. The size of the granules can be tailored for a predetermined end use application by the nature and amount of the particular agent selected. For instance, siliceous materials such as diatomaceous earth, Cab-O-Sil® and Hi-Sil® tend to produce a small mesh granular product which, upon drying, can be readily resuspended into a sprayable formulation. Coarser agents such as corn cob grits, pregranulated starch, etc. will yield a larger mesh particulate product for field application in granular form.

The amount of the granulating agent will typically be in the range of about 5–20% by weight of the total product, with a preferred range of about 10–16% by weight.

Optional Oil Component:

Incorporating an oil into the formulation has been found to enhance the storage stability and field viability of certain living biocontrol agents. Moreover, the oil unexpectedly enhances the effectiveness of the granulation agent to convert the dough-like mass into discrete particles. Suitable oils include mineral oil and vegetable oils, such as those derived from corn, soybean, sunflower, safflower, rapeseed, cottonseed and the like. Usually the oil would constitute less than about 20% by weight of the total composition.

Formulation Protocol:

The biocontrol agent suspension, the water absorbent agent, and the membrane stabilization agent can be blended together in any order and by any conventional means in the art. In addition, the membrane stabilization agent can be prepared in an aqueous solution and used as a suspending agent for the biocontrol agent. The optional oil component is preferably added last, for the reason that it could otherwise interfere with the ability of the water absorbent to absorb the free water in the suspension as previously discussed.

The primary components are blended together into a dough-like mass in a Sigma mixer or the like, and thereafter the granulating agent is added. Blending is continued until the dough "crumbs" and is recoverable as wet granules. The granules can thereafter be dried by any known method which will not adversely affect the viability of the biocontrol agent. Though air drying is usually preferred, under appropriate situations, mild oven drying could also be used. Thus, by appropriate selection of component ratios as within the skill of a person in the art, it is possible to recover particles of granulated biocontrol agent of the desired size without the need for grinding.

Other Components:

Besides the primary components described above, other additives and adjuncts may be formulated into the subject compositions. Examples of these include dispersants, feeding stimulants (phagostimulants), UV protectants, preservatives, and inert fillers. Also of interest are agronomically acceptable carriers or vehicles for the active agent or any of the other components formulated into the granular compositions.

In accordance with one embodiment of the invention, the granules are resuspended in water, an oil-in-water emulsion, or an invert emulsion (water-in-oil) for field application as a sprayable liquid. In yet another embodiment of the invention, the granulated biocontrol agent can be applied to the plant foliage or soil as a dry formulation. In either form, the flowable nature of the product lends itself to field application using conventional equipment without the need for specialized modification.

Pests:

The target pests contemplated for control by means of the subject granulated agents of the invention include all species susceptible to the above-mentioned biocontrol agents. Such pests include insects, weeds, crop diseases, detrimental nematodes and the like. The granulated agents find application for field crops, orchard crops, ornamentals and certain stored agricultural products.

The granulated agents of the invention may be stored at room temperatures for extended periods of time with minimal loss of vitality. For instance, the survival rate of *Pseudomonas syringae* granulated as described in the examples and stored at 22° C. for 202 days was approximately 85%. At −15° C., the survival exceeded 95%.

It should be understood that living organisms are very fragile and sensitive to environmental conditions. Even with the advantages achieved by the present invention, the skilled artisan will appreciate that some organisms will not be effective against specific targets and that the effectiveness of some granulated organisms will be a function of the specific environmental conditions. However, it would be within the skill of a person in the art to determine the effectiveness of candidate organisms and formulations for a particular end use application.

The following examples are intended only to further illustrate the invention and are not intended to limit the scope of the invention which is defined by the claims.

EXAMPLE 1

Evaluation of the Effect of Temperature on the Storage Viability of *P. syringae* pv. *tabaci* Granulated in Accordance with the Invention.

Bacterial isolate 94–19 was obtained from diseased leafy spurge (*Euphorbia esula* L.) growing in native rangeland. This strain was identified as *Pseudomonas syringae* pv. *tabaci* by GC FAMES. The isolate was grown for two days on King's medium B (KB) [King, E. O., M. K. Ward, and D. E. Raney (1954), Two Simple Media for the Demonstration of Pyocyanin and Fluorescein, *J Lab. Clin. Med.* 44:301–307] at 22° C. Individual plates were harvested by adding 10 ml 0.1 M potassium phosphate buffer (PB) pH 7.0 and scraping with a sterile cotton swab. The harvested bacteria were pooled together and buffer was added to yield a total volume equivalent to 37.5 ml per harvested plate. The bacterial suspension was serially diluted to $10_7$ and plated onto KB using a spiral plater to determine bacterial population.

Four replicate batches of *P. syringae* pv. *tabaci* were formulated in a starch/oil/sucrose matrix then mixed with fumed silica using the following procedures. Ten g water-absorbent starch (Water-lock®, Grain Processing Corporation, Muscatine, Iowa) was mixed with 10 ml unrefined corn oil (Spectrum Naturals, Inc. Petaluma, Calif.), microwaved on high for thirty seconds then allowed to cool to room temperature. The bacterial suspension (37.5 ml) was added and mixed with a spatula until all of the suspension was absorbed by the starch and a cohesive dough-like ball was formed. Thirty-nine g sucrose (confectioners sugar, G & W Branch, Western Sugar Co., Denver, Colo.) was added to this mixture and blended, followed by 13 g amorphous-fumed silica (Cab-O-Sil®, Cabot Corp., Tuscola, Ill.). Blending was continued until the dough crumbed, thereby producing a granular product. The resulting mixture was spread in foil pans to a depth of approximately 0.5 cm and dried in a laminar flow hood for 48 hours at room temperature. The dried formulation was then sieved using 25, 60 and 100 mesh sieves. The portion which passed through the 60 mesh and was retained on the 100 mesh sieve was used for sampling. The four replicate batches were divided into three samples each and stored at −15° C., 2° C. and 22° C. The results are reported in Table I, below.

EXAMPLE 2

Determination of the Effects of Sucrose and Oil, Independently and in Combination, on the Survival of Granulated *Pseudomonas syringae* pv. *tabaci*.

The experimental design was a 2×2 factorial with three replications. Treatments were as follows: (−)sucrose(−)oil, (−)sucrose(+)oil, (+)sucrose(−)oil, (+)sucrose(+)oil and were based on the following standard formulation.

5 ml unrefined corn oil 5 g Water-lock® absorbent starch 20 ml bacterial suspension 20 g sucrose 6.5 g Cab-o-Sil®

Formulations were prepared as described above in Example 1, except mixing operations were performed with a 'mini food-processor' (handy chopper, Black and Decker, Inc. Shelton, Conn.). Samples were evaluated over a 228 day period. The results are reported in Table II, below.

EXAMPLE 3

Determination of the Effects of Sucrose and Oil, Independently and in Combination, on the Survival of Granulated *Fusarium oxysporum*.

A strain of *Fusarium oxysporum* pathogenic to Canada thistle (*Circium arvense*) was cultured in potato dextrose broth amended with an infusion of Canada thistle leaves for 7 days on a rotary shaker. The mycelial and spore suspension was concentrated approximately 2× by pouring the culture into coffee filters which had been placed in a bed of water-absorbent starch (Grain Processing Corporation, Muscatine, Iowa).

The procedure and formulation of Example 2 was repeated except that *Fusarium oxysporum* was substituted for the *Pseudomonas syringae* pv. *tabaci*. The concentration of the organism in the initial inoculum was adjusted according to the total weight of the nonaqueous components in order to provide a constant population of biocontrol agent per dry weight of product across all trial formulations. The results are reported in Table III, below.

EXAMPLE 4

Evaluation of the Effect of Sucrose Level on Survival of *P. syringae* pv. *tagetis*.

*P. syringae* pv. *tagetis*, a pathogen of Canada thistle (*Cirsium arvense*(L.)Scop.), was grown using the method described in Example 1 for *P. Syringae* pv. *tabaci*. Individual plates were harvested in 8 ml PB and centrifuged 30 min. at 3000 rpm's in a Sorvall RT 6000® refrigerated centrifuge at 80° C. Pellets were resuspended in PB and pooled together for a volume equivalent to 2.5 mls per harvested plate. Initial population was determined as described in Example 1.

Four rates of sucrose (0×, 0.25×, 0.5×, and 1×, based on the standard formulation given above in Example 2), either with or without the oil, were combined in a factorial experiment to determine the optimal rate of sucrose for survival of *P. syringae* pv. *tagetis* over time. The concentration of the organism in the initial inoculum was adjusted to the total weight of the nonaqueous components in order to provide a constant population of biocontrol agent per dry weight of product across all trial formulations. One full replication of the experiment was prepared at a time, with three replications completed within a 1 week period. All formulations were dried and sieved as above except the fraction remaining on the 60 mesh sieve was used for sampling. Previous experiments (not reported) indicated slightly higher viability in the 60 mesh sieve vs. the 100 mesh fraction.

The results are reported in Table IV, below.

EXAMPLE 5
Evaluation of the Effect of Oil Level on Survival of *P. syringae* pv. *tagetis*.

The procedure of Example 4 was repeated, except this time the sucrose level was held constant at 1×, and the level of oil was tested at four rates (0×, 0.25×, 0.5×, and 1×). The concentration of the organism in the initial inoculum was adjusted according to the total weight of the nonaqueous components in order to provide a constant population of biocontrol agent per dry weight of product across all trial formulations. The results are reported in Table V, below.

EXAMPLE 6
Granulated *Fusarium oxysporum* Formulation and Pathogenicity Assay on Sweet Potato.

Fungal growth. *Fusarium oxysporum* f. sp. *batas*, a pathogen of sweet potato, was grown on shake culture (4 flasks containing 100 ml fungal solution) in Czapeks medium with yeast extract plus 100 ppm kanamycin sulfate, for 10 days. Conidial suspension was alternately washed and concentrated by centrifugation with two sterile distilled water rinses (approx. concentration $1 \times 10^8$ microconidia/ml).

Formulation. Concentrated conidia were hydrated to 75 ml and 8 g of hydrated silica were added to suspend the conidia. The mixture was combined with 150 mg streptomycin sulfate for bacterial control. In a separate container, 20 ml of unrefined corn oil, 20 gm Water-lock® (potassium salt) as a water absorbent and 7.5 gm bacto-peptone (Difco) were mixed and heated in the microwave for 30–40 seconds. The hydrated conidial suspension was blended in equal volumes (1:1) with the cooled Water-lock®:corn oil:peptone mixture and then combined with powder sugar equal to 65% by weight (approx. 130 gm powder sugar to 200 ml volume). The conidia:sugar suspension was slowly stirred while adding Cab-O-Sil® (M5)(approx. 19.22 gm) to absorb the oil and until the mixture was reduced to a powdered product consisting of fine granules. The powdered formulation was allowed to dry in the clean air chamber for 48 hrs and sieved to further break up the granules. The dry product yield was approx. 250 gm.

Conidial concentration; storage survival. *Fusarium conidia* concentration in the dry formulated product was determined on a selective media for *F. oxysporum* f. sp. *batas* referred to as Komada's media [Nelson, P. E., T. A. Toussoun, and W. F. O. Marass (1983), Fusarium species. An Illustrated Manual for Identification, Pennsylvania State University]. A serial dilution of the dry product was plated on Komada media and an individual colony was considered to be the product of one conidium. Data were reported as colony forming units (CFU) per gram of dry product.

Initial concentration of formulated product was calculated to be in the range of 7 to $24 \times 10^6$ CFU/gram. The product was separated on a #60 mesh fraction ($7 \times 10^6$ CFU/gm) and a #100 mesh fraction ($24 \times 10^6$ CFU/gm). Initial spore concentration was $1 \times 10^{8-9}$/ml of water. The loss in conidia concentration during formulation was $1 \times 10^2$/ml or gm, considering the weight of formulated product equal to water.

Upon storage of the formulated product at room temperature in a plastic Zip-lock® for a period of 15 months, spore concentration was $1 \times 10^6$ CFU/gm for the #60 mesh fraction and $1 \times 10^5$ CFU/gm for the #100 mesh fraction.

Product efficacy in a plant assay. The granulated product prepared above was compared to non-formulated conidial suspension for pathogenicity on sweet potato cultivar 'Porto Rico' in a pot assay. Sweet potato cuttings were rooted and soaked in a suspension of the dry granulated product (0.1 gm/10 ml phosphate buffer) for 10 min. Rooted cuttings were soaked in a conidia suspension ($1 \times 10^6$ conidia/ml by direct spore count) as a comparison for the dry granulated product of the invention. Non-inoculated plants were used as the control. The dry granulated formulation and the conidial suspension caused similar plant symptoms on sweet potato, including plant stunting, reduced root growth and early signs of wilting after 4 wks. The control plants were healthy and displayed no symptoms of the disease.

EXAMPLE 7

Survival of *Colletotrichum gloeosporioides* NRRL 21046 in the Standard Formulation of Example 2.

Preparations of a mycoherbicidal fungus, *Colletotrichum gloeosporioides* NRRL 21046, pathogenic to coffee senna and sicklepod were prepared by combining conidida and mycelial fragments from vegetable juice broth. The procedure of Example 2 was repeated, substituting the *C. gloeosporioides* preparation for the bacterial suspension in the standard formulation. Dried samples of the formulation were stored under conditions of refrigeration (4° C.) and at room temperature (22° C.).

The results are reported in Table VI, below.

Bioassays of the formulation described above were performed by spraying coffee senna seedlings at 40 days intervals. Ten grams of each preparation were suspended in 100 ml sterile water and sprayed until runoff occurred on coffee senna seedlings that were in the cotyledonary growth stage. Treated plants were placed in dew chambers at 25° C. and 100% relative humidity for 16 h, and then transferred to the greenhouse at 28° C. and incubated for 14 days. The results at 0, 40, 120, 200 and 240 days are repor ted in Table VII, below.

TABLE 1

Effect of temperature on survival of *Pseudomonas syringae* pv. tabaci in a sucrose/oil granular formulation

| Temperature | Days in Storage | | | | |
|---|---|---|---|---|---|
| ° C. | 0 | 28 | 129 | 220 | 365 |
| −15 | 9.441 | 9.47 | 9.16 | 9.43 | 9.20 |
| 2 | 9.44 | 9.40 | 9.11 | 9.21 | 8.91 |
| 22 | 9.44 | 9.24 | 8.53 | 7.40 | 5.93 |

[1]Data values represent $Log_{10}$ colony forming units/g formulation

TABLE II

Effect of oil and sucrose on survival of *Pseudomonas syringae* pv. tabaci in a granular formulation

| Treatment | Days in Storage (22° C.) | | | |
|---|---|---|---|---|
| | 0 | 28 | 112 | 228 |
| S−O− | 9.99[1] | 9.17 | 7.97 | 6.86 |
| S−O+ | 10.07 | 10.1 | 9.43 | 8.54 |
| S+O− | 10.00 | 9.49 | 9.20 | 8.51 |
| S+O+ | 10.30 | 9.71 | 9.20 | 8.59 |

[1]Data values represent $Log_{10}$ colony forming units/g formulation

TABLE III

Effect of oil and sucrose on survival of *Fusarium oxysporum* in a granular formulation

| Treatment | Days in Storage (22° C.) | | | |
|---|---|---|---|---|
| | 0 | 28 | 56 | 114 |
| S−O− | 5.51 | 5.87 | 5.31 | 4.73 |
| S−O+ | 6.52 | 6.42 | 5.63 | 4.87 |
| S+O− | 7.2 | 7.12 | 6.72 | 5.42 |
| S+O+ | 7.34 | 7.27 | 6.87 | 4.46 |

[1]Data values represent $Log_{10}$ colony forming units/g formulation

TABLE IV

Survival of *Pseudomonas syringae* pv tagetis in a granular formulation at four rates of sucrose

| Sucrose level | | Days in Storage (22° C.) | | | |
|---|---|---|---|---|---|
| X[a] | % by wt.[b] | 0 | 40 | 84 | 202 |
| without oil | | | | | |
| 0 | 0 | 9.38 | 8.66 | 8.26 | 6.23 |
| 0.25 | 30.3 | 9.56 | 9.04 | 8.98 | 8.11 |
| 0.5 | 46.5 | 9.65 | 9.34 | 9.07 | 7.81 |
| 1 | 63.5 | 9.57 | 9.39 | 9.2 | 8.25 |
| with oil (1.0 X[a]) | | | | | |
| 0 | 0 | 9.79 | 8.99 | 8.57 | 6.66 |
| 0.25 | 23.8 | 9.41 | 8.84 | 9.32 | 8.18 |
| 0.5 | 38.4 | 9.35 | 9.16 | 8.84 | 7.99 |
| 1 | 55.5 | 9.45 | 9.19 | 8.89 | 7.99 |

[a]Factor relative to amount in standard formulation
[b]Dry weight basis, calculated as the percentage of the total weight of the sucrose, Water-lock ®, and Cab-o-Sil ®

TABLE V

Survival of *Pseudomonas syringae* pv tagetis in a granular formulation at four rates of oil

| Oil level | Days in Storage (22° C.) | | | |
|---|---|---|---|---|
| (X[a]) | 0 | 40 | 84 | 202 |
| 0 | 9.57 | 9.39 | 9.2 | 8.25 |
| 0.5 | 9.48 | 9.23 | 8.81 | 7.93 |
| 1.0 | 9.45 | 9.19 | 8.89 | 7.99 |
| 1.5 | 9.33 | 9.23 | 8.84 | 8.03 |

[a]Factor relative to amount in standard formulation

TABLE VI

Survival of *Colletotrichum gloeosporioides* NRRL 21046 in the standard granular formulation of Example 2

| Storage Temperature | Days in Storage | | | | |
|---|---|---|---|---|---|
| (° C.) | 0 | 40 | 120 | 200 | 240 |
| 4 | 5.0 | 4.99 | 4.90 | 4.76 | 4.69 |
| 22 | 5.0 | 4.83 | 4.71 | 3.90 | 2.50 |

[1]Data values represent $Log_{10}$ colony forming units/g formulation

TABLE VII

Bioassay of *Colletotrichum gloeosporioides* NRRL 21046 granular formulation

| Storage Temperature | Days in Storage Plant Mortality (%) | | | | |
|---|---|---|---|---|---|
| (° C.) | 0 | 40 | 120 | 200 | 240 |
| 4 | 100 | 89 | 80 | 74 | 70 |
| 22 | 100 | 80 | 60 | 55 | 52 |

We claim:

1. A granular biocontrol formulation comprising: (1) a biocontrol agent for an agricultural pest selected from the group consisting of insects, weeds, crop diseases, and detrimental nematodes, said agent being pathogenic upon contact or ingestion by said pest and selected from the group consisting of bacteria, fungi, viruses, microsporidians, protozoa, nematodes and pathogenic components of said agents; (2) a water absorbent material; (3) a membrane stabilization agent; and (4) a granulating agent, wherein the biocontrol agent is in aqueous suspension, wherein the water absorbent material binds with available water in the suspension of biocontrol agent, wherein the amount of membrane stabilization agent is in the range of about 10–65% by dry weight of the complete formulation and wherein the aqueous suspension of biocontrol agent, the water absorbent material, the membrane stabilization agent and the granulating agent exist in said formulation as a blended mixture.

2. The granular biocontrol agent formulation of claim 1, wherein said water absorbent material is a starch graft copolymer.

3. The granular biocontrol agent formulation of claim 1, wherein said membrane stabilization agent is sucrose.

4. The granular biocontrol agent formulation of claim 1, wherein said granulating agent is a siliceous material.

5. The granular biocontrol agent formulation of claim 1, wherein said biocontrol agent is a living pathogen selected from the group consisting of bacteria, fungi, viruses, microsporidians, protozoa and nematodes.

6. The formulation of claim 1 wherein said formulation is a dry mixture.

7. The formulation of claim 1 wherein said formulation is a sprayable dispersion.

8. The formulation of claim 7 wherein said sprayable dispersion is an oil-in-water emulsion or a water-in-oil emulsion.

9. A method of preparing a biocontrol agent in a granular formulation, wherein said biocontrol agent is pathogenic upon contact or ingestion by an agricultural pest selected from the group consisting of insects, weeds, crop diseases, and detrimental nematodes and wherein said agent is selected from the group consisting of bacteria, fungi, viruses, microsporidians, protozoa, nematodes and pathogenic components of said agents, comprising the steps:

a. blending said biocontrol agent in aqueous suspension with a water absorbent material and a membrane stabilization agent into a dough;

b. blending the dough of step (a) with a granulating agent to reduce said dough to discrete granules;

c. recovering the granules of step (b).

10. The method of claim 9 and further comprising blending said biocontrol agent with an oil in an amount of less than 20% by weight of the granular formulation.

11. The method of claim 10 wherein said oil is blended with the biocontrol agent after the biocontrol agent is blended with the water absorbent material.

12. The method of claim 9 wherein the granules recovered in step (c) are dried.

13. The method of claim 9 wherein said water absorbent material is a starch graft copolymer.

14. The method of claim 9 wherein said membrane stabilization agent is sucrose.

15. The method of claim 9 wherein said granulating agent is a siliceous material.

16. The method of claim 9 wherein said biocontrol agent is a living pathogen selected from the group consisting of bacteria, fungi, viruses, microsporidians, protozoa and nematodes.

17. The method of claim 9 wherein the granules recovered in step (c) are redispersed in water to yield a sprayable formulation.

18. The method of claim 9 wherein the granules recovered in step (c) are redispersed in an oil-in-water emulsion or a water-in-oil emulsion.

* * * * *